(12) United States Patent
Bailly et al.

(10) Patent No.: US 9,801,704 B2
(45) Date of Patent: Oct. 31, 2017

(54) PROTHESIS COMPRISING A REINFORCED MESH

(75) Inventors: Pierre Bailly, Caluire (FR); Genevieve Doucet, Villefranche sur Seone (FR)

(73) Assignee: Sofradim Production, Trevoux (FR)

( * ) Notice: Subject to any disclaimer, the term of this patent is extended or adjusted under 35 U.S.C. 154(b) by 844 days.

(21) Appl. No.: 13/519,068

(22) PCT Filed: Dec. 15, 2010

(86) PCT No.: PCT/EP2010/069693
§ 371 (c)(1),
(2), (4) Date: Dec. 4, 2012

(87) PCT Pub. No.: WO2011/073225
PCT Pub. Date: Jun. 23, 2011

(65) Prior Publication Data
US 2013/0079803 A1 Mar. 28, 2013

(30) Foreign Application Priority Data

Dec. 16, 2009 (FR) ...................................... 09 59082

(51) Int. Cl.
*A61F 2/02* (2006.01)
*A61F 2/00* (2006.01)
*A61B 17/08* (2006.01)

(52) U.S. Cl.
CPC ............ *A61F 2/0063* (2013.01); *A61B 17/08* (2013.01); *A61F 2210/0004* (2013.01); *A61F 2250/0031* (2013.01)

(58) Field of Classification Search
CPC ............ A61F 2/0063; A61F 2002/0068; A61F 2250/0031; A61F 2/105; A61F 2210/0004; A61B 17/08

USPC .................... 623/23.72–23.75; 606/151, 213
See application file for complete search history.

(56) References Cited

U.S. PATENT DOCUMENTS

| | | | | |
|---|---|---|---|---|
| 5,766,246 | A | * | 6/1998 | Mulhauser et al. .......... 606/151 |
| 6,669,735 | B1 | * | 12/2003 | Pelissier ............... A61F 2/0063 606/151 |
| 2003/0181988 | A1 | * | 9/2003 | Rousseau ................... 623/23.72 |
| 2009/0082792 | A1 | * | 3/2009 | Koyfman et al. ............ 606/151 |
| 2009/0259235 | A1 | * | 10/2009 | Doucet et al. ............. 623/23.72 |

(Continued)

FOREIGN PATENT DOCUMENTS

| | | |
|---|---|---|
| EP | 0 614 650 A2 | 9/1994 |
| FR | 2 929 834 A1 | 10/2009 |

(Continued)

OTHER PUBLICATIONS

International Search Report corresponding to International Application No. PCT/EP2010/069693, completed on Jan. 17, 2011 and dated Jan. 25, 2011; 3 pages.

*Primary Examiner* — Diane Yabut
*Assistant Examiner* — Erich Herbermann

(57) ABSTRACT

The present invention relates to a prosthesis (200) comprising a flexible mesh (1), which is delimited by a peripheral outer edge (1*a*), and a reinforcing element for said mesh, characterized in that said reinforcing element comprises at least one sheet of semi-rigid and flexible material defining a continuous vaulted structure (201) that has an inner face (201*a*) and an outer face (201*b*), at least the base (201*d*) of said vaulted structure being fixed to the peripheral outer edge of said mesh.

15 Claims, 4 Drawing Sheets

(56) References Cited

U.S. PATENT DOCUMENTS

Figure 1:
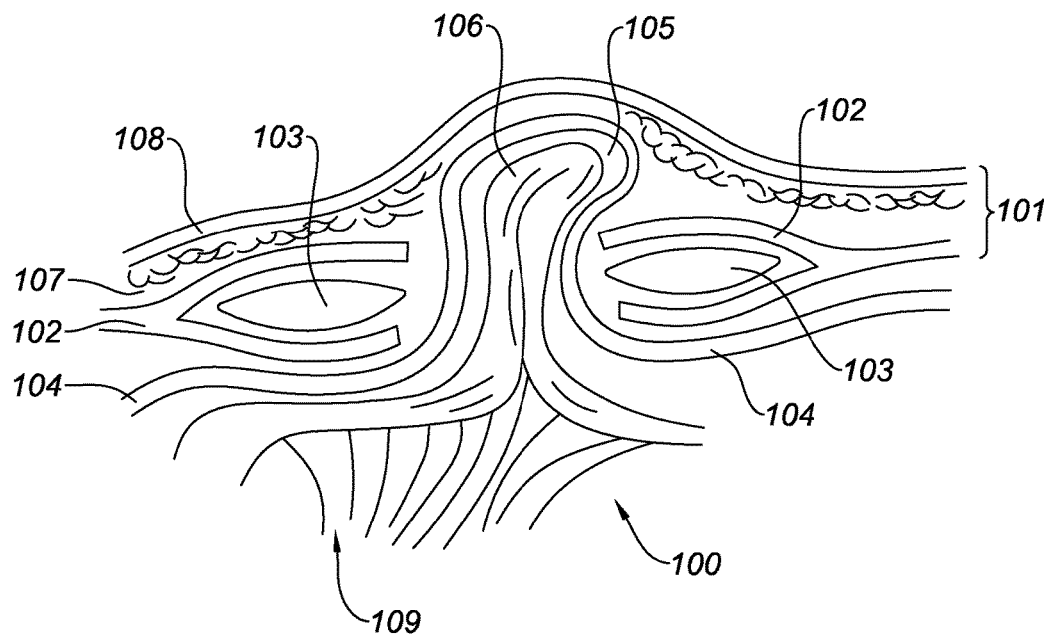

2009/0270999 A1* 10/2009 Brown .................. A61F 2/0063
 623/23.72
2010/0292717 A1* 11/2010 Petter-Puchner ..... A61F 2/0063
 606/151
2010/0292718 A1* 11/2010 Sholev et al. ................ 606/151

FOREIGN PATENT DOCUMENTS

| WO | WO 00/07520 A1 | 2/2000 |
| WO | WO 2007/038934 A1 | 4/2007 |
| WO | WO 2008/055028 A1 | 5/2008 |
| WO | WO 2009/027542 A1 | 3/2009 |

* cited by examiner

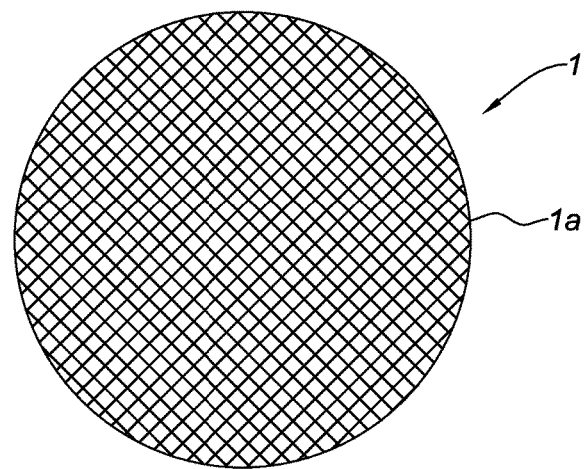
Fig. 3
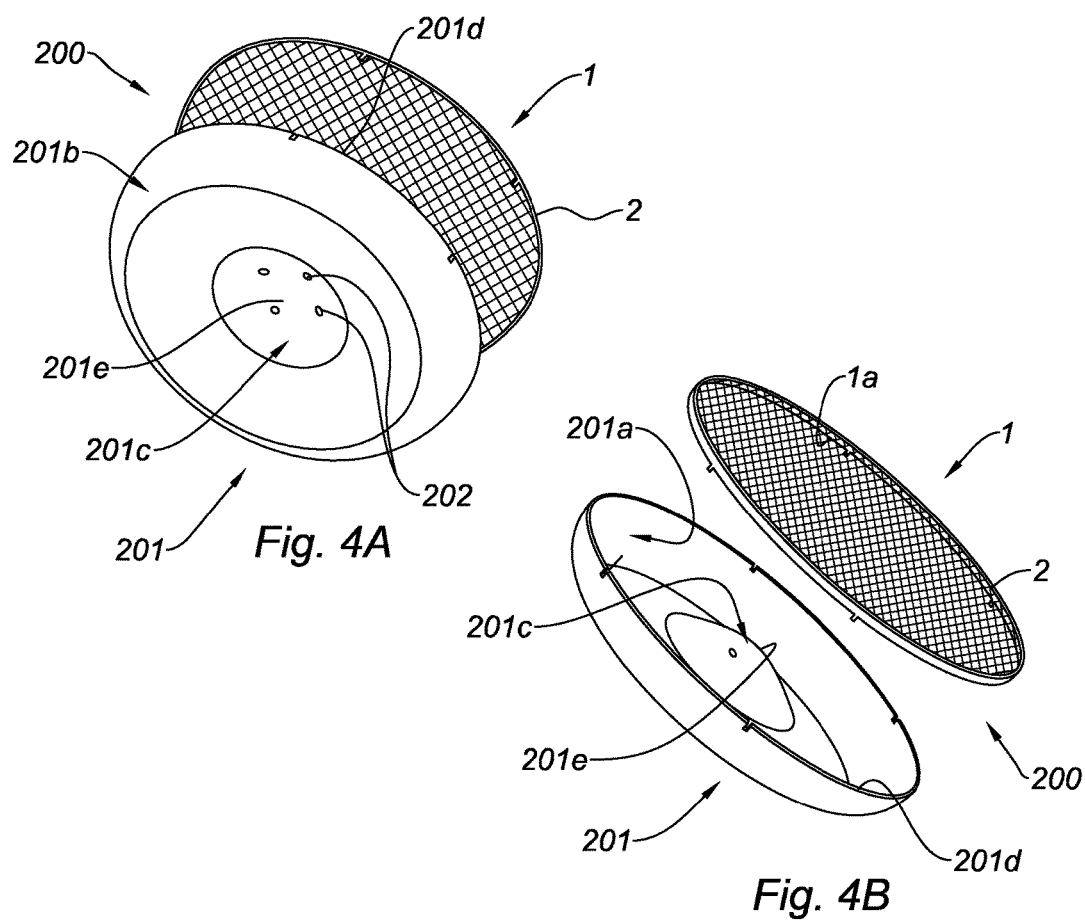
Fig. 4A
Fig. 4B

PROTHESIS COMPRISING A REINFORCED MESH

CROSS-REFERENCE TO RELATED APPLICATIONS

This application is a U.S. National Stage Application filed under 35 U.S.C. §371(a) of International Application No. PCT/EP2010/069693 filed Dec. 15, 2010, which claims the benefit of and priority to French Application Serial No. 09/59082 filed Dec. 16, 2009, the entire contents of which are incorporated by reference herein.

The present invention relates to a prosthesis, for example a prosthesis for plugging hernias, comprising a mesh and a reinforcing element for this mesh.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias or incisional hernias (a hernia occurring through a parietal surgical scar) show themselves in the form of a bulge at the surface of the skin and are classed, for example, as umbilical or inguinal hernias or incisional hernias, depending on where they are located.

In order to repair a hernia defect, surgeons often fit a prosthesis in place which is made of synthetic mesh and replaces or strengthens the weakened anatomical tissues.

However, a prosthesis of this kind, once implanted, is subjected to an abdominal pressure that tends to push it outwards. Such pressure can cause reversion of the prosthesis and lead to risks of the hernia recurring.

The effectiveness of the prosthesis, hence the ability to minimize the risks of recurrence, thus depends to a large extent on how well the prosthesis is fixed. In particular, before being fixed, the prosthesis has to be correctly spread out against the abdominal wall that it is intended to strengthen. This is because the prostheses of the mesh type, that is to say based on an arrangement of filaments forming a textile, are generally flexible. In order to introduce them into the hernia orifice, they are often folded up to reduce their volume. They therefore tend to form creases on the abdominal wall when introduced at the implantation site. Their spreading out is of key importance in this respect but can prove difficult, particularly when treating an umbilical hernia which, being smaller than an inguinal hernia, offers the surgeon very little space in which to manipulate the prosthesis.

For example, in the case of umbilical hernias, or when seeking to repair trocar holes, or else in preventive treatment, the size of the defect to be treated is small, for example 1 to 3 cm in diameter, and it is conceivable to perform open surgery. However, in this type of surgery, the surgeon has little space to work in and has a poor view of the hernia. He must therefore preferably have at his disposal a prosthesis that is easy to position, spread out and fix, if possible avoiding the need to suture the periphery of the prosthesis, which is a complicated and difficult procedure to perform under these working conditions.

If the prosthesis is not perfectly spread out against the abdominal wall, there is a risk of the peritoneal sac being caught and also a risk of a soft organ being inserted between the prosthesis and the abdominal wall, which can lead to risks of adherence, pain and intestinal occlusion and can increase the possibility of recurrence. It is therefore essential for the surgeon to ensure that no part of the prosthesis is folded and that no viscera or part of the intestine is caught between the prosthesis and the abdominal wall. Moreover, poor positioning of the sutures or poor fixing of the prosthesis risks deforming the prosthesis and creating tension.

Thus, particularly in the case of an umbilical hernia with a small orifice for introducing the prosthesis, it would be advantageous to have a prosthesis that is able, under stress, to occupy a small volume so as to facilitate its introduction into the abdominal cavity through said orifice, and which can then be easily deployed, spread out and flattened against the abdominal wall, even automatically without the need for any great manipulation of the prosthesis by the surgeon.

Various prostheses are available that can be folded up and then deployed.

For example, document WO-A-00/07520 discloses a prosthesis composed of a flexible mesh reinforced by a double hoop provided with spokes. A thread passed through the periphery of the larger hoop allows the prosthesis to be shaped into a truncated cone at the moment it is introduced into the inguinal orifice. However, spreading the prosthesis out and flattening it against the abdominal wall once it has been introduced at the implantation site requires significant work on the part of the surgeon and is somewhat unsatisfactory. Moreover, there is nothing to avoid the risks of reversion of the prosthesis once the latter has been implanted and is subjected to the abdominal pressure that tends to push it outwards.

The present invention concerns a prosthesis that can be folded up at least partially in order to reduce the volume that it occupies during its introduction into a small incision and that can also be spread out and easily fixed, said prosthesis being configured in such a way that the risks of reversion of said prosthesis are avoided once it has been implanted, this prosthesis being subjected to the abdominal pressure that tends to push it outwards.

The prosthesis according to the invention is used for treating a hernia defect of the abdominal wall, in particular for treating umbilical hernias in which the size of the hernia defect is small.

A first aspect of the present invention concerns a prosthesis comprising a flexible mesh, which is delimited by a peripheral outer edge, and a reinforcing element for said mesh, characterized in that said reinforcing element comprises at least one sheet of semi-rigid and flexible material defining a continuous vaulted structure that has an inner face and an outer face, at least the base of said vaulted structure being fixed to the peripheral outer edge of said mesh.

Within the meaning of the present application, "vaulted structure" is understood as a hollow structure having the overall shape of a cone or of a dome, it being possible for the cone or the dome to be axisymmetric, pyramid-shaped, ellipsoid or of any other shape, for example constructed on a polygonal or square plane. For example, a structure having the shape of a sugarloaf is also included as a vaulted structure within the meaning of the invention. Moreover, the cone or the dome of the vaulted structure of the prosthesis according to the invention can have a central part of lesser curvature than the rest of the structure, for example being substantially flat. Alternatively, the central part can be inverted, that is to say its curvature is inverted in relation to the curvature of the rest of the structure, in such a way as to form a hollow shape at the vertex of the dome.

Within the meaning of the present application, by "continuous vaulted structure" is meant that the sheet of material forming the vaulted structure is continuous and free of significant voids. As will appear in the description below, the sheet of material forming the vaulted structure may contain discrete orifices of less than 1 mm diameter for example, each capable of receiving a thread or a filament for example, but it is free of significant voids such as access ports for a tool or for the finger of a surgeon.

By virtue of its flexible structure, the vaulted structure has a certain elasticity that allows it to deform under the effect of certain particular stresses and to recover its semi-rigid rest configuration once these stresses have been relaxed.

Within the meaning of the present application, a "mesh" is understood as an arrangement of biocompatible filaments, such as a knit, a woven, a nonwoven, preferably open-worked, that is to say provided with pores that favour recolonization of tissue. Such a mesh can be bioresorbable, permanent or partially bioresorbable. It is in general sufficiently flexible to be folded up at the time of introduction into the abdominal cavity. The mesh can be made up of one layer of textile or of several layers. Such meshes are well known to a person skilled in the art. The mesh that can be used according to the invention can be supplied in any form whatsoever, rectangular, square, circular, oval, etc., and then be cut to suit the shape of the hernia defect. For example, the overall shape of the mesh can be circular or oval, in which case the vaulted structure preferably has a cone or dome structure that is axisymmetric, ellipsoid or any other shape. Alternatively, the mesh can have a generally square shape or a rectangular shape, in which case the vaulted structure according to the invention preferably has a structure in the form of a pyramid-shaped cone or dome.

As will become apparent from the description that follows, the prosthesis according to the invention is not subject to the phenomenon of reversion. This is because the semi-rigid vaulted structure allows the prosthesis to be kept pressed flat against the abdominal wall, avoiding any reversion of the prosthesis.

In one embodiment of the invention, the vertex of the vaulted structure is situated opposite the centre of said mesh.

For example, said vaulted structure is substantially conical.

Alternatively, said vaulted structure has the shape of a dome.

In some embodiments, the central part of said dome can be inverted.

In one embodiment, the central part of said vaulted structure is provided with at least one centring filament.

Alternatively, several centring filaments can be fixed to the vertex of the vaulted structure. In other embodiments, the centring filament or filaments can be replaced by textile tapes. This or these centring filament(s) or tape(s) can, for example, be of use to the surgeon in making it easier to position the prosthesis at the centre of the defect to be treated and to bring together the margins of the defect such that they can be sutured.

In one embodiment, said mesh conforms to the inner face of said vaulted structure.

In another embodiment, substantially only the base of said vaulted structure is fixed to the peripheral outer edge of said mesh, said mesh being kept flat and spread out in the plane formed by the base of said vaulted structure. The mesh is thus pressed perfectly flat against the abdominal wall when the prosthesis is implanted.

In one embodiment, the outer face of said vaulted structure is covered by a non-stick coating, particularly in order to avoid the formation of undesired and serious post-surgical fibrous adhesions.

Within the meaning of the present application, "non-stick" is understood as a smooth and non-porous biocompatible material or coating that does not offer space for cell recolonization.

In one embodiment, said semi-rigid and flexible material is bioresorbable. For example, this material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof.

Alternatively, said rigid and flexible material is non-bioresorbable and is chosen from among polypropylenes, polyesters such as polyethylene terephthalates, polyamides, silicones, polyether ether ketone (PEEK), polyarylether ether ketone (PAEK) and mixtures thereof.

Figure 2:
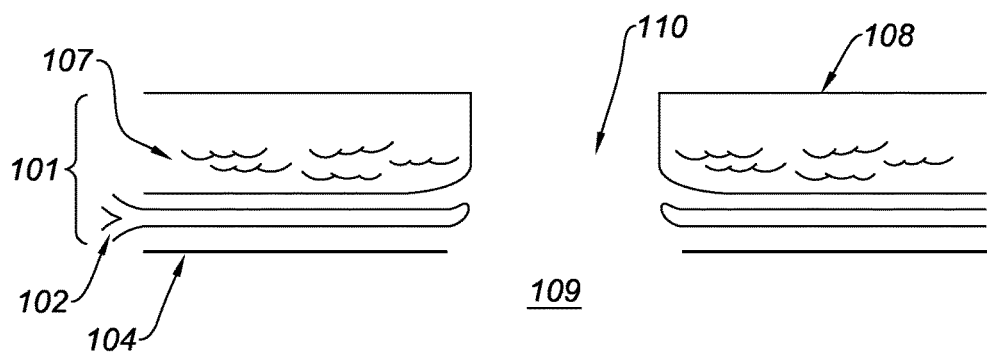
Figure 5:
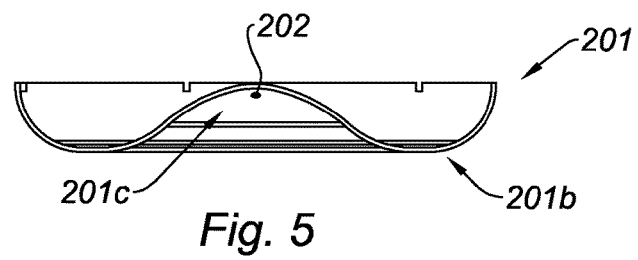
Figure 6:
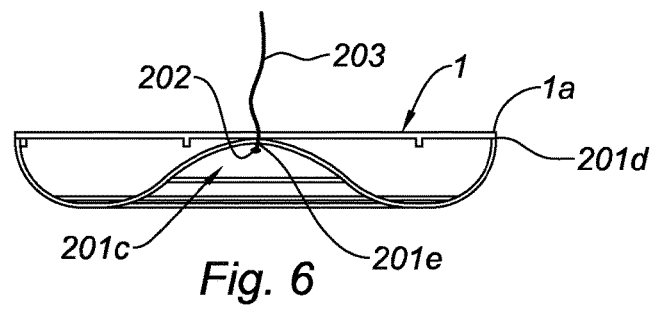
Figure 7:
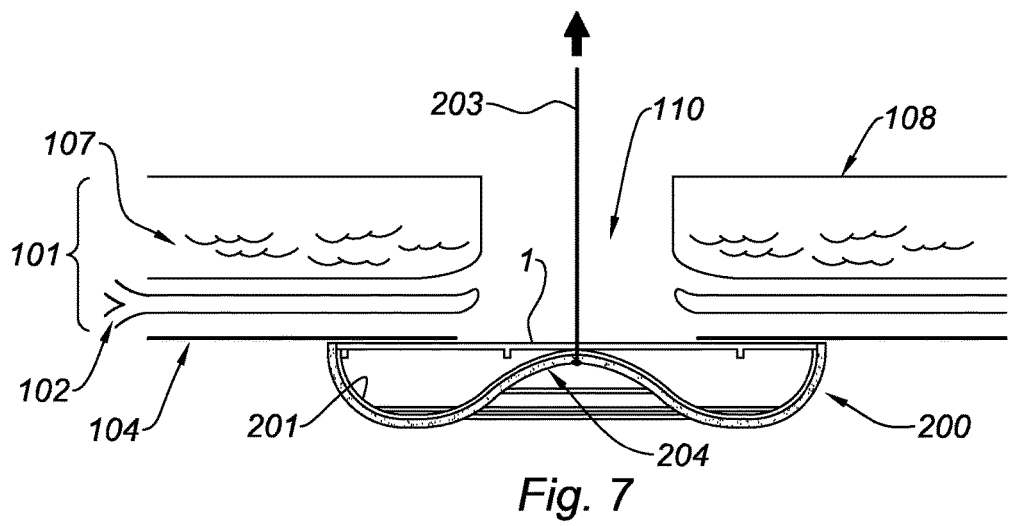
Figure 8:
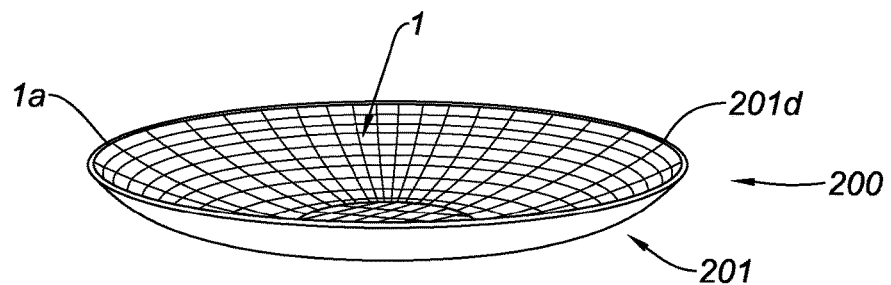
Figure 9:
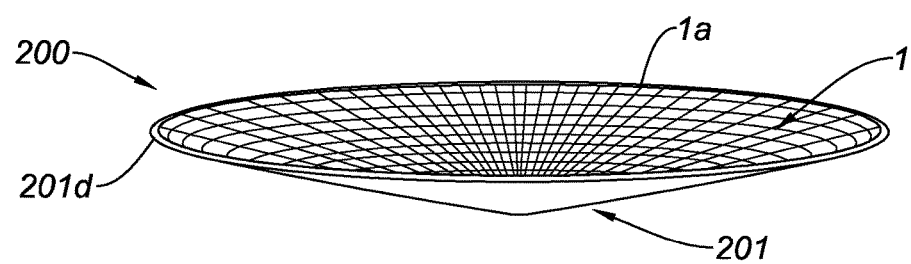

The present invention will become clearer from the following description and from the attached drawings in which:

FIG. 1 is a sectional view of a median abdominal hernia or incisional hernia,

FIG. 2 is a simplified view of the hernia in FIG. 1 once the surgeon has made an abdominal incision, FIG. 3 is a plan view of an embodiment of a mesh for a prosthesis according to the invention, FIGS. 4A and 4B are exploded perspective views, respectively from below and from above, of an embodiment of the prosthesis according to the invention, FIG. 5 is a sectional view of the vaulted structure of the prosthesis from FIGS. 4A and 4B, FIG. 6 is a sectional view of the prosthesis from FIGS. 4A and 4B, FIG. 7 is a sectional view of the prosthesis from FIG. 6, covered on its outer face with a non-stick coating and placed at the implantation site, FIG. 8 is a perspective view of another embodiment of the prosthesis according to the invention, FIG. 9 is a perspective view of another embodiment of the prosthesis according to the invention.

FIG. 1 shows a hernia defect 100 in the abdominal wall 101, which is characterized by a break in continuity of the fascia 102 surrounding the rectus muscles 103 and by a protrusion of the peritoneum 104 forming a sac, and the hernia sac 105 containing either fat (epiploon) or part of the viscera 106 and therefore pressing on the fatty tissue 107 and lying flush with the skin 108. Treatment of a hernia defect 100 involves repositioning the viscera 106 in the abdominal cavity 109 and keeping them there.

FIG. 2 shows the hernia defect 100 from FIG. 1 once the surgeon has made an incision in the skin 108, the abdominal wall 101 and the peritoneum 104 in order to reduce the hernia sac 105. The viscera are not shown in FIG. 2: they have been pushed back into the abdominal cavity 109. The surgeon must now introduce into the abdominal cavity 109, via the incision 110 that he has made, a prosthesis designed to strengthen the abdominal wall, before closing the incision 110 using sutures for example. In the case of an umbilical hernia, the size of the incision 110 is particularly small, for example of the order of 1 to 3 cm in diameter.

FIG. 3 shows a mesh 1 of circular shape which can be used for a prosthesis according to the invention, for example the one described in FIGS. 4A and 4B.

The mesh 1 is made up of an arrangement of biocompatible filaments, such as a knit, a woven or a nonwoven. It can be bioresorbable, permanent or partially bioresorbable. Generally, the mesh is open-worked and contains pores for better integration of tissue. This mesh 1 is generally sufficiently flexible to be folded up at the time of introduction into the abdominal cavity 109 via the incision 110. In general, however, the mesh is a textile that does not have an elasticity allowing it to spontaneously recover a spread-out configuration once it has been folded up. The mesh 1 can be composed of one layer of textile or of several layers. The textile can be a two-dimensional or three-dimensional knit. Such meshes are well known to a person skilled in the art and are not described in further detail here. The mesh can be supplied in the form of a strip which is cut to the dimensions of the defect that is to be treated. In the example shown, the mesh 1 has a circular shape, tailored to the shape of the incision 110 for the hernia defect 100, and delimited by a peripheral outer edge 1a. In other embodiments, the shape of the mesh could be oval. Alternatively, the mesh can have a rectangular or square shape, in which case the vaulted structure of the prosthesis according to the invention can be in the shape of a pyramid-shaped dome or cone.

Referring to FIGS. 4A and 4B, these show a prosthesis 200 according to the invention, comprising a mesh 1 and a reinforcing element in the form of a sheet of material defining a continuous vaulted structure 201: the vaulted structure 201 has an inner face 201a and an outer face 201b. In the example shown, the vaulted structure 201 has the shape of a dome whose central part 201c is inverted. In other words, as can be seen from FIGS. 4A and 4B and from FIG. 5, the curvature of the central part 201c of the vaulted structure 201 is inverted in relation to the curvature of the rest of the structure 201, such that the central part 201c defines a hollow shape in the outer face 201b of the vaulted structure 201. Finally, the vaulted structure 201 comprises a base 201d opposite its vertex 201e. In the example shown, the base 201d of the vaulted structure 201 has the shape of a circle, the dome defined by the vaulted structure 201 being axisymmetric. In other embodiments not shown, the dome could be constructed on a square or polygonal plane, and the base of the vaulted structure would then be a square or a polygon.

As appears form these Figures, the vaulted structure is made of a continuous sheet of material: in other words, the vaulted structure is not an open structure, it is free of significant voids or holes, in particular voids or holes allowing the passage of a tool or of the finger of a surgeon. In particular, the central part of the vaulted structure is continuous with the rest of the vaulted structure.

In the example shown, the vaulted structure 201 is provided with four discrete orifices 202 which, as will become clear later in the present description, permit the passage of one or more centring filaments intended to help the surgeon position the prosthesis in relation to the hernia defect and then fix said prosthesis to the abdominal wall. These discrete orifices 202 constitute anchor points of the centring filaments and usually are less than 1 mm diameter.

In another embodiment not shown, the vaulted structure could be provided at its vertex with a single discrete orifice.

The continuous vaulted structure is preferably provided with at least two discrete orifices, more preferably with at least three or four discrete orifices, situated in the central part of the vaulted structure but offset in relation to the vertex thereof: the presence of several discrete orifices, and therefore of several centring filaments, allows the surgeon to balance the tension between the various centring filaments when positioning the prosthesis and to better centre the prosthesis in relation to the defect that is to be plugged.

The vaulted structure 201 is made of a continuous sheet of semi-rigid and flexible material. According to the present application, "semi-rigid and flexible" is understood as meaning that although the vaulted structure is deformable under the action of specific stresses, such as a centripetal pressure applied in order to fold it substantially on itself, it nevertheless adopts and maintains at rest, that is to say in the absence of stress, a defined form having substantially a vault shape. In particular, because of its shape and the nature of the material from which it is made, the vaulted structure of the prosthesis according to the invention has an elasticity that allows it to recover its defined vault shape after relaxation of a pressure aimed at temporarily deforming it.

The materials that may be suitable for producing the vaulted structure of the prosthesis according to the invention can be chosen from any biocompatible material having a degree of rigidity and a degree of elasticity allowing it to meet the requirements described above.

The vaulted structure 201 can thus be made of any biocompatible material, either bioresorbable or non-bioresorbable. In a preferred embodiment, it is made of bioresorbable material. In the present application, "bioresorbable" is understood as the characteristic whereby a material is absorbed by the biological tissues and disappears in vivo after a given period of time which can, for example, vary from one day to several months, depending on the chemical nature of the material.

Thus, as bioresorbable materials suitable for producing the vaulted structure of the prosthesis according to the present invention, mention may be made of polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. As bioresorbable material suitable for producing the vaulted structure of the prosthesis according to the invention, mention may be made of the polyester (glycolide, dioxanone, trimethylene carbonate) available commercially from Covidien under the trade name Biosyn® or the polyester (glycolide, caprolactone, trimethylene carbonate, lactide) available commercially from Covidien under the trade name Caprosyn®.

As non-bioresorbable materials suitable for producing the vaulted structure of the prosthesis according to the present invention, mention may be made of polypropylenes, polyesters such as polyethylene terephthalates, polyamides, polyether ether ketone (PEEK), polyarylether ether ketone (PAEK) and mixtures thereof.

The vaulted structure of the prosthesis according to the invention can, for example, be made in one piece by injection moulding one or more biocompatible thermoplastics. Alternatively, the vaulted structure can be produced by bonding several films of resorbable or non-resorbable materials, and hot compression of several layers of textiles, as long as the resulting sheet forming the vaulted structure is continuous as defined in the present application.

The material used to produce the vaulted structure 201 can be non-stick. Alternatively or in combination, the vaulted structure 201 of the prosthesis 200 can be covered with a non-stick coating 204 on its outer face 201b so as to avoid in particular the formation of undesired and serious post-surgical fibrous adhesions, as is shown in FIG. 7; once the prosthesis 200 is implanted, the outer face 201b of the vaulted structure 201 is situated opposite the abdominal cavity 109.

The non-stick material or coating is chosen from among bioresorbable materials, non-bioresorbable materials and mixtures thereof. The non-bioresorbable non-stick materials can be chosen from polytetrafluoroethylene, polyethylene glycols, polysiloxanes, polyurethanes, stainless steels, derivatives of precious metals and mixtures thereof.

Said non-stick material or coating is preferably bioresorbable: the bioresorbable materials suitable for said non-stick coating can be chosen from collagens, oxidized celluloses, polyacrylates, trimethylene carbonates, caprolactones, dioxanones, glycolic acid, lactic acid, glycolides, lactides, polysaccharides, for example chitosans, polyglucuronic acids, hyaluronic acids, dextrans and mixtures thereof.

The non-stick coating makes it possible to protect the mesh 1 of the prosthesis 200, at least during the initial phase of healing, that is to say the mesh 1 is protected from exposure to inflammatory cells such as granulocytes, monocytes, macrophages or even the multi-nuclear giant cells that are generally activated by the surgery. Indeed, at least during the initial phase of healing, the duration of which can vary between 5 and 10 days approximately, only the non-stick coating can be accessed by the various factors such as proteins, enzymes, cytokines or cells of the inflammatory line, in the area of the mesh.

In the case when the non-stick coating is made of non-resorbable materials, it thus protects the mesh 1 before and after implantation, throughout the period of implantation of the prosthesis 200.

Moreover, by virtue of the non-stick coating, the fragile surrounding tissues such as the hollow viscera, for example, are protected particularly from the formation of undesired and serious post-surgical fibrous adhesions.

In the case when the non-stick material comprises a bioresorbable material, it is preferable to choose a bioresorbable material that is resorbed only after a few days, so as to ensure that the non-stick coating can perform its function of protecting the intestine and the hollow organs during the days after the operation and until the cell recolonization of the prosthesis in turn protects the fragile organs.

In the example shown in FIGS. 4A and 4B, the mesh 1 is provided with a collar 2 fixed to the peripheral outer edge 1*a*. This collar 2, which must be able to be folded and/or deformed, is preferably semi-rigid and is made, for example, of the same material as is used to produce the vaulted structure 201. This collar 2 is intended to facilitate the fixing of the mesh 1 to the base of the vaulted structure 201, as can be seen in FIG. 6.

Referring to FIG. 6, the latter shows a sectional view of the prosthesis 200 from FIGS. 4A and 4B once the mesh 1 has been fixed to the base 201*d* of the vaulted structure 201. As will be seen from this figure, in the example shown only the base 201*d* of the vaulted structure 201 is fixed to the peripheral outer edge 1*a* of the mesh 1, the latter being kept flat and spread out in the plane formed by the base 201*d* of the vaulted structure 201. The centre of the mesh 1 lies opposite the vertex 201*e* of the vaulted structure 201.

The mesh 1 can be fixed to the base 201*d* of the vaulted structure 201 by ultrasonic welding of the collar 2 to the base 201*d*. Alternatively, for example when the collar 2 is not present, the peripheral outer edge 1*a* of the mesh can be bonded to the base 201*d* of the vaulted structure 201.

The vaulted structure 201 can be fixed to the mesh 1 by any method that ensures a reliable join of the mesh 1 and of the vaulted structure 201. For example, the vaulted structure 201 can be adhesively bonded, welded, for example by ultrasonic welding, or sewn onto the mesh 1.

FIG. 6 also shows a centring filament 203 passing through a discrete orifice 202. The prosthesis can already be equipped with this centring filament when supplied to the surgeon. Alternatively, the surgeon can himself fit this centring filament, and possibly other filaments, just before carrying out the surgical intervention.

By virtue of its elasticity, the continuous vaulted structure 201 can adopt a configuration in which it is substantially folded up on itself, under the effect of a centripetal radial stress. Thus, when the surgeon wishes to implant the prosthesis 200, he applies a pressure to the outer face 201*b* of the vaulted structure in the centripetal radial direction; the whole prosthesis then folds up on itself in order to occupy a smaller volume, and this makes it easier for the surgeon to introduce the prosthesis into the hernia orifice 110 (cf. FIG. 2).

The mesh 1 and the non-stick coating 204 (see FIG. 7) are sufficiently flexible to follow the successive deformations of the vaulted structure 201 of the prosthesis 200 when the latter is introduced into the implantation site.

Having made the incision 110 described in FIG. 2, the surgeon uses his fingers or a clamp to apply a centripetal radial stress to the prosthesis 200 covered with a non-stick coating 204 on the outer face of the vaulted structure 201, in order to fold the prosthesis 200 on itself and introduce it into the abdominal cavity 109, with the vertex 201*e* of the vaulted structure 201 directed toward the abdominal cavity 109.

Once the prosthesis 200 is in the abdominal cavity 109, the surgeon relaxes the centripetal radial pressure that he was exerting thereon. By virtue of its elasticity, the vaulted structure 201, and therefore the prosthesis 200, recovers its rest configuration, as is described in FIG. 6. The prosthesis 200 thus deploys automatically in the abdominal cavity 109, the outer face 201*b* of the vaulted structure 201, covered with the non-stick coating 204, being directed towards the abdominal cavity 109, and the mesh 1 being perfectly tensioned and spread out.

In a next step, the surgeon uses the centring filament(s) 203, preferably located in the area of the central part of the vaulted structure, both to centre the prosthesis 200 with respect to the incision 110 and to press the prosthesis 200 firmly against the abdominal wall 101, 104. To do this, he pulls significantly on the centring filament 203 as shown in FIG. 7. During this step, the surgeon can pull on the centring filament 203 without fear of risking a reversion of the prosthesis 200 since, by virtue of the particular shape of the continuous vaulted structure 201 of the prosthesis 200, and by virtue of the fact that the vaulted structure 201 is continuous and fixed at least to the peripheral outer edge 1*a* of the mesh 1, the latter, and therefore the prosthesis 200, cannot revert (that is to say reintroduce itself into the orifice 110). In other words, the central part of the vaulted structure, which is part of the continuous sheet of material forming the vaulted structure, can not collapse and reintroduce itself into the orifice 110. Thus, the more the surgeon pulls on the centring filament 203 placing the latter under tension, the more the vaulted structure 201 presses the mesh 1 onto the abdominal wall 101, 104, with the mesh 1 conforming to the shape of the latter.

The mesh 1 is therefore perfectly spread out, and there is no risk of the viscera becoming interposed between the mesh 1 and the abdominal wall 101, 104.

All that the surgeon then has to do is to suture the centring filament(s) 203 to the abdominal wall 101, 104, closing up the incision 110. As can be seen in FIG. 7, the prosthesis 200 is thus perfectly deployed, spread out and pressed firmly against the abdominal wall 101, 104 without risk of viscera becoming trapped between the prosthesis and the abdominal wall 101, 104. If the vaulted structure 201 is bioresorbable, a resorption time is chosen that is sufficient to allow the mesh 1 to be recolonized before the vaulted structure 201 disappears. Fixation of the mesh 1 is thus assured over the long term.

The prosthesis according to the invention is particularly easy to fit in place. This fitting is also particularly reliable, avoiding any risk of viscera being trapped and any risk of reversion of the prosthesis. A prosthesis according to the invention is particularly suitable for treating umbilical hernias, for which the abdominal incision made is of small size. Indeed, the prosthesis according to the invention is able to adopt a configuration in which it occupies a particularly small volume allowing it to be introduced easily into the abdominal cavity via a small incision, and without requiring the use of a special ancillary device. By virtue of its particular structure, the prosthesis according to the invention deploys automatically in the abdominal cavity without the intervention of an additional tool. Again by virtue of its particular structure, the prosthesis according to the invention can be spread out and pressed firmly against the abdominal wall effectively, again without requiring the intervention of a specific tool to assist with the spreading out, and without risk of reversion of the prosthesis. The prosthesis according to the invention thus permits effective, simple and rapid treatment of a hernia, particularly an umbilical hernia, minimizing the risks of a recurrence.

FIGS. 8 to 9 show other embodiments of the prosthesis according to the invention.

FIG. 8 shows a perspective view of an alternative form of the prosthesis 200 described in FIGS. 4A and 4B, in which the continuous vaulted structure 201 is an axisymmetric dome whose central part is not inverted, and in which the mesh 1 conforms to the inner face of the continuous vaulted structure 201. Thus, the mesh 1 is preferably fixed, for example by adhesive bonding, to the whole surface area of the inner face of the continuous vaulted structure 201. During placement of the prosthesis 200, one or more centring filaments (not shown) extending from the central part of the vaulted structure 201 allow the surgeon to press the base 201d of the vaulted structure 201 firmly against the abdominal wall, thereby avoiding insertion of viscera between the mesh 1 and the abdominal wall.

FIG. 9 shows a perspective view of an alternative form of the prosthesis described in FIGS. 4A and 4B, in which the continuous vaulted structure 201 is an axisymmetric cone and in which the mesh 1 conforms to the inner face of the continuous vaulted structure. Thus, the mesh 1 is preferably fixed, for example by moulding, on the whole surface area of the inner face of the vaulted structure 201. During placement of the prosthesis 200, one or more centring filaments (not shown) extending from the central part of the continuous vaulted structure 201 allow the surgeon to press the base 201d of the vaulted structure 201 firmly against the abdominal wall, thereby avoiding insertion of viscera between the mesh 1 and the abdominal wall.

In the two embodiments described in FIGS. 8 and 9, the centre of the mesh 1 is situated opposite the vertex of the dome or cone, respectively, defining the continuous vaulted structure 201.

It goes without saying that the method of placement described above would apply in the same way to the prostheses in FIGS. 8 and 9.

Thus, the prostheses 200 in FIGS. 8 and 9 are placed with the mesh 1 facing the abdominal wall, and with the continuous vaulted structure facing the abdominal cavity. The outer face of the continuous vaulted structure can be covered with a non-stick coating.

The prosthesis according to the invention is useful in the treatment of hernias, particularly umbilical hernias, in which the size of the hernia defect is small. The geometry of the prosthesis according to the invention, the semi-rigid and at the same time flexible nature thereof, and the possibility of fixing this prosthesis centrally in relation to the hernia that is to be plugged, make it possible to avoid reversion of the prosthesis in the hernia once the prosthesis is implanted.

The invention claimed is:

1. A prosthesis comprising a flexible mesh, which is delimited by a peripheral outer edge, and a reinforcing element for said mesh, wherein said reinforcing element comprises at least one sheet of semi-rigid and flexible material defining a continuous vaulted structure that has an inner face and an outer face, at least a base of said continuous vaulted structure being fixed to said peripheral outer edge of said mesh, wherein a central surface of said continuous vaulted structure is an inverted continuous structure.

2. The prosthesis according to claim 1, wherein a vertex of the continuous vaulted structure is situated opposite a center of said mesh.

3. The prosthesis according to claim 1, wherein said continuous vaulted structure has a certain elasticity that allows the continuous vaulted structure to deform under a particular stress and recover the semi-rigid configuration after the particular stress is removed.

4. The prosthesis according to claim 1, wherein said continuous vaulted structure has the shape of a dome.

5. The prosthesis according to claim 1, wherein the central surface of said continuous vaulted structure is provided with at least one centering filament.

6. The prosthesis according to claim 1, wherein said mesh conforms to the inner face of said continuous vaulted structure.

7. The prosthesis according to claim 1, wherein substantially only the base of said continuous vaulted structure is fixed to the peripheral outer edge of said mesh, said mesh being kept flat and spread out in a plane formed by the base of said continuous vaulted structure.

8. The prosthesis according to claim 1, wherein the outer face of said continuous vaulted structure is covered with a non-stick coating.

9. The prosthesis according to claim 1, wherein said semi-rigid and flexible material is bioresorbable.

10. The prosthesis according to claim 9, wherein said bioresorbable material is selected from the group consisting of polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof.

11. The prosthesis according to claim 1, wherein said semi-rigid and flexible material is non-bioresorbable and is selected from the group consisting of polypropylenes, polyesters, polyamides, silicones, polyether ether ketone (PEEK), polyarylether ether ketone (PAEK) and mixtures thereof.

12. The prosthesis according to claim 1, further comprising a deformable collar fixed to said peripheral edge of the mesh to fix the mesh to the base.

13. The prosthesis according to claim 1, wherein a portion of the central surface of the continuous vaulted structure comprises from zero to four discrete orifices.

14. The prosthesis according to claim 1, wherein a portion of the central surface of the continuous vaulted structure comprises a single discrete orifice.

15. The prosthesis according to claim 1, wherein a portion of the central surface of the continuous vaulted structure comprises at least two discrete orifices.

* * * * *